United States Patent [19]

Hambitzer et al.

[11] Patent Number: 5,597,473
[45] Date of Patent: Jan. 28, 1997

[54] PROCESS FOR THE DETECTION OF NITROTOLUENES

[75] Inventors: Gunther Hambitzer, Pfinztal; Winfried Boke, Karlsruhe, both of Germany

[73] Assignee: Fraunhofer-Gesellschaft zur Forderung der angewandten Forschung e.V., Munich, Germany

[21] Appl. No.: 372,327

[22] Filed: Jan. 13, 1995

[30] Foreign Application Priority Data

Jan. 14, 1994 [DE] Germany .................. 44 00 859.7

[51] Int. Cl.⁶ ................................................ G01N 27/26
[52] U.S. Cl. ................ 205/780.5; 204/400; 204/412; 204/434; 205/787
[58] Field of Search .................. 204/153.1, 153.14, 204/400, 434; 205/780.5, 787

[56] References Cited

U.S. PATENT DOCUMENTS

| | | | |
|---|---|---|---|
| 2,805,191 | 9/1957 | Itersch | 204/402 |
| 3,071,530 | 1/1963 | Neville | 204/415 |
| 3,402,116 | 9/1968 | Kaltenhauser et al. | 204/402 |
| 3,406,109 | 10/1968 | Molloy | 204/415 |
| 3,526,577 | 9/1970 | Molloy | 204/415 |
| 4,132,605 | 1/1979 | Tench et al. | 204/434 |

OTHER PUBLICATIONS

Kolthoff et al, *Polarography*, 1952, pp. 145, 146, 215, 250, 339, 624, 750, 751 month unavailable.

*Primary Examiner*—T. Tung
*Attorney, Agent, or Firm*—Antonelli, Terry, Stout & Kraus, LLP

[57] ABSTRACT

A process for detecting nitrotoluenes, particularly trinitrotoluene, dinitrotoluene and derivatives of nitrotoluenes in soils, liquids and gases is proposed and a voltage is applied to an electrode which is in contact with an electrolytic solution having the substance to be tested, the voltage being reduced for producing a reduction reaction and increased for producing an oxidation reaction and the current intensity of at least a residual current and an anodic current maximum occurring is determined, particularly as a function of the voltage applied.

18 Claims, 3 Drawing Sheets

PROCESS FOR THE DETECTION OF NITROTOLUENES

FIELD OF THE INVENTION

The invention relates to a process for the detection of nitrotoluenes, particularly trinitrotoluene, dinitrotoluene and derivatives of nitrotoluenes, in the soil, liquids and gases, as well as to an apparatus for performing such a process.

BACKGROUND OF THE INVENTION

The detection and in particular the identification of trinitrotoluene (TNT), dinitrotoluene (DNT) and nitrotoluenes (NT), as well as derivatives thereof, particularly when investigating soils for detecting scrapped armaments in the countryside or the area around explosives enterprises is of great importance. Although frequently only areas of a few square kilometres at individual, unknown locations are contaminated with TNT pockets with a size of square meters, it has hitherto generally been necessary to completely remove the soil of the uncontaminated areas. This is in particular due to the fact that the known analysis methods are expensive and lead to considerable time expenditure. It is necessary to take samples from the area, which can then only be analysed after approximately one hour at the analytical location provided for this purpose. Thus, a precise demarcation of the contaminated area is only possible in this way with considerable time and labour costs. The known analytical apparatuses for TNT determination also require approximately one hour for testing a sample. As in addition the disposal costs rise significantly with the volume of the contaminated excavated material, either a time-consuming determination of the precise contaminated soil area is necessary, or possibly too much soil must be removed with the resulting disposal costs.

However, it is not only necessary to test soils, but also liquids with respect to contamination with TNT, DNT, NT and derivatives thereof, because waste, seepage and ground waters can become contaminated by soil containing the aforementioned substances or by the soil cleaning processes. Once again at present only relatively time-consuming expensive processes are available, such as gas chromatography.

In addition, most explosive charges are made from TNT or with the addition of TNT due to the technologically simple production and processability. As such explosives are also used in blackmail or terrorist threats and attacks, the discovery of such explosives, e.g. in luggage and passenger checks at airports and the like represents an important task in order to prevent danger to human life. However, a rapid and uncomplicated detection of mines is indispensable when searching for plastic-enveloped mines.

The TNT used in the manufacture of explosives is a solid giving off small quantities of vapour to the environment. However, this vapour can only be detected with very complicated and costly methods, such as gas chromatography with mass spectrometry.

The problem of the invention is therefore to provide a process and an apparatus for identifying such contaminations in the soil, liquids and gases, which is characterized by a simple, rapid and inexpensive detection of TNT, DNT and NT in situ and also contaminations of varying concentrations can be reliably and simply detected in the most varied substances, such as soils, liquids, etc.

SUMMARY OF THE INVENTION

According to the invention this problem is solved in the case of a process of the aforementioned type, which is characterized in that a voltage is applied to an electrode, which is in contact with an electrolytic solution containing the substance to be tested, the voltage is reduced for producing a reduction reaction and then increased for producing an oxidation reaction and the current intensity of at least one residual current and an anodic current maximum which occurs is determined in particular as a function of the voltage applied. An apparatus according to the invention is characterized in that said apparatus has a sensor element with three electrodes, namely a working electrode, a reference electrode and a counterelectrode and that the electrodes are connected to a regulatable voltage source.

As a result of the process and apparatus according to the invention it is possible to test the most varied soils contaminated in the subppm to 100% range with TNT and DNT for the said materials, because the nitro groups of DNT and TNT are initially reduced on the working electrode. TNT, DNT and NT, as well as derivatives thereof in each case form for the particular contamination specific reduction products, whose oxidation behaviour can be investigated by raising the voltage. The same applies for contaminations dissolved in liquids, as well as dinitrotoluene (DNT) and trinitrotoluene (TNT) in gases, which at ambient temperature have an equilibrium vapour pressure of 55,700 or 9,400 ppt. As such an apparatus can be constructed in a very compact and portable manner, it can be used directly in situ. Sampling and sample testing, between which one hour elapses in the prior art, are rendered unnecessary.

Within the framework of the invention fundamentally all voltammetry processes are usable. As a rule working takes place with d.c. voltage, the current intensity being determined as a function of the set voltage between the working electrode and a counterelectrode. The voltage is reduced, preferably continuously from a starting value. After reaching a lower value there is then once again a preferably continuous increase. In this way so-called voltammograms are obtained in the form of current-voltage curves making it possible to establish whether there has been a reduction of the contaminations such as TNT, DNT or NT, as well as an oxidation of their reduction products.

On reaching a fixed upper value the applied voltage is again reduced in order to produce a reduction at the working electrode.

As a result the reduction behaviour of the particular redox pair formed by the reduction products is rendered determinable by measuring the current-voltage curve.

After reaching the starting voltage preferably a measuring cycle is terminated. As the current peaks occurring at the working electrode for the reduction and oxidation of the redox pairs are at different voltages for the different contaminations, it is possible to determine through the position thereof at the end of a measuring cycle which contaminations are contained in the soil, liquids and gases. As a result of the level of the current-voltage curve or the area below it, a measure for the concentration of DNT, TNT, NT and derivatives thereof is provided. Thus, the determination of such contaminations can be carried out without difficulty when performing the process according to the invention. By fixing the voltage range traversed during a measuring cycle it is possible to exclude reactions of disturbing substances such as combat materials or decomposition products and/or substances dissolved in liquid or gases and vapours produced artificially or naturally occurring in air. The process is characterized by a high selectivity and has no cross-sensitivity relative to the disturbing substances.

According to a particularly preferred embodiment of the process initially a voltage is applied at a level where in the case of the compounds to be detected a double layer area forms, that the voltage is raised to a reverse potential of more than 1 V, that the current intensity of the residual current occurring in the double layer area is measured, that the voltage is then reduced for producing a reduction reaction, that the voltage value of a resulting cathodic current maximum is determined, that for producing an oxidation reaction the voltage is raised again, that the voltage value is determined at which an anodic current maximum occurs, that the value of the anodic current maximum is determined and that the quotient of the value of the anodic current maximum and the measured value of the residual current is determined as a value representative of the nitrotoluene content of the substance to be tested. The anodic current maximum has a positive sign and the cathodic current maximum a negative sign.

The starting voltage is preferably applied with approximately 500 to 900 mV, advantageously approximately 700 mV and said value is in the double layer area. The increase advantageously takes place up to a reverse potential of the measuring electrode of approximately 1.3 to 1.5 V.

According to a preferred development, particularly in a first pass, after reaching the cathodic current maximum the voltage is reduced by approximately a further 300 mV.

Preferably the voltage is further increased above the value at which the anodic current maximum occurs and in particular up to the end of the double layer area. It is therefore advantageous to raise the voltage by approximately 700 mV above the voltage at which the anodic current maximum occurs or up to approximately 1300 mV.

The voltages are in particular continuously or quasi-continuously changed. The potential is generally changed at speeds between 100 mV/sec and a few V/sec, such as 5 V/sec.

Preferably there is a passage through a voltage range of 1 V per second. The total time taken for a measuring cycle is max. 2 sec. It is also possible in this way to simply and rapidly investigate further areas or TNT, DNT and NT-containing pockets with an order of magnitude of square meters. It is ensured that no excessive soil quantity is removed and consequently the disposal costs can be greatly reduced, because a demarcation of the contaminated area is readily possible due to the large number of measurements which can be performed every minute.

Preferably different voltage ranges are covered. In this way it is possible with the aid of such rapid cyclic measurements to selectively reduce and detect NT, DNT and TNT. Preferably current-voltage curves of different voltage ranges are superimposed. Through such an appropriate superimposing of current-voltage curves in an extended voltage range, which includes the NT reduction, with the current-voltage curves for the DNT and/or TNT determination in the voltage ranges covered, it is possible to quantitatively detect NT in the presence of DNT and TNT.

According to further developments following a measuring cycle the electrodes are multiply polarity reversed for cleaning the working electrode. As a result of the rapid switching between oxygen and hydrogen evolution the coating forming on the working electrode is removed. Alternatively or in combination with the multiple polarity reversal the surface of the working electrode is periodically cleaned after a measuring cycle or also permanently, preferably by a mechanical scraper or sliding wiper. A combination of both cleaning methods is preferable if high concentrations of TNT or DNT and/or deactivating disturbing substances are contained in the substance being investigated. Without such a cleaning the electrode would become deactivated and the level of the current peaks would decrease, so that the measured results would be falsified.

In order to be able to perform the process according to the invention in a substance whose pH-value is not sufficiently low, the area surrounding the working electrode is acidified. In the case of continuous measurements it is also provided that a liquid substance to be tested is moved passed the electrode system with the working electrode and preferably the liquid substance is passed through a flow cell.

As DNT and TNT have an equilibrium vapour pressure of 55,700 or 9,400 ppt at ambient temperature, for the selective identification of these substances, together with NT and the derivatives thereof into the ppt range, a gaseous substance is moved passed a liquid-impermeable, but gas-permeable diaphragm, through which the gaseous substance passes into the electrolytic solution. Preferably the gaseous substance is moved passed the diaphragm by pumping. Highly developed, complicated equipment both with regards to the mechanics, sensor means and electronics, such as are required for the known gas chromatography procedure are no longer required. In addition, a continuous measurement can be performed.

In order to increase the transition of TNT or DNT and NT, etc. from the gaseous into the liquid phase, preferably a difficultly volatile co-solvent is added to the electrolytic solution. In order to increase the reaction speed and therefore the response time, prior to performing a measuring cycle the electrolytic solution is preferably heated.

The formation of the TNT reduction product and the path of the TNT reduction current independently of the composition of the substance to be tested, as well as the unambiguous connection between TNT reduction and oxidation of the reduction product, characterized by the level and the potential position of the anodic current peaks, are not trivial and cannot be foreseen and are consequently unexpected and surprising.

The current measured at potentials below 500 mV is in general a superimposing of currents, which can be attributed to the reduction and sometimes also oxidation of electrochemically reactive substances unknown as regards type and concentration. Thus, a direct measurement of the TNT reduction current as a measure for the TNT concentration is not possible.

In addition, according to the invention, the use of the said process for the detection of nitrotoluenes, particularly trinitrotoluene, dinitrotoluene and derivatives thereof in soils, liquids and gases is provided.

The working electrode is preferably an electrode which at least contains gold. A possible embodiment of the working electrode is in the form of a double pin electrode, whilst in another embodiment it is a ring electrode.

The reference electrode is preferably a platinum electrode, which has the characteristics of a reversible hydrogen electrode due to the supply or cathodic evolution of hydrogen. The reference electrode can be a platinum wire or a platinum pin.

According to further developments the electrodes are immersed in an electrolytic solution in which the substance to be tested is dissolved. This is necessary for performing the process according to the invention. The electrolytic solution is preferably sulphuric or phosphoric acid. The gold and platinum electrodes are not attacked by these acids.

For the investigation of liquid and gaseous substances, according to further developments below the sensor element is provided a flow cell. This makes it possible to perform continuous measurements on liquid and gaseous substances. This flow cell is preferably constructed in such a way that it can be screwed onto the sensor element. Therefore it is possible to use the same sensor element in different environments and for different substances, namely soils, gases and liquids. If necessary, the flow cell is screwed onto the sensor element. This makes it possible to selectively and reliably measure with a single apparatus contaminations in soils, liquids and gases.

According to further developments for the investigation of gases with respect to a contamination, the flow cell is separated by a liquid-impermeable, but gas-permeable diaphragm from the sensor element and the electrolytic solution. Although in this way the gas can penetrate the electrolytic solution, an exit of electrolytic fluid into the flow cell is prevented. The pore size is preferably 40 nm and directly on the side of the pores remote from the flow cell is located the working electrode.

According to further developments, for the pumping of the gas through the flow cell a pumping mechanism is provided, so that a continuous measurement can take place.

According to another preferred embodiment, the sensor system has a regulating and evaluating electronics. Thus, from the current values measured at the applied voltage values, it is possible to determine the concentrations of TNT, DNT, NT and derivatives thereof. Preferably there is an output unit for concentration indication or display purposes, so that the concentration can be directly read off during measurement. In a further development the apparatus has an alarm unit for giving an alarm signal on exceeding a predetermined concentration value.

Preferably a device is provided for reactivating at least the working electrode. For this purpose, it is possible to provide below the electrodes, a scraper or a sliding wiper for cleaning the electrode surface.

The scraper or sliding wiper ensures that the working electrode is always cleanable in a simple manner for obtaining reproducible measured results. This is necessary, because it is deactivated by the measurement and a coating forms on the electrode which must be removed.

BRIEF DESCRIPTION OF THE DRAWINGS.

Further advantages and features of the invention can be gathered from the claims and the following description of an embodiment of the invention with reference to the drawings, wherein show:

DETAILED DESCRIPTION OF THE DRAWINGS.

Figure 1:
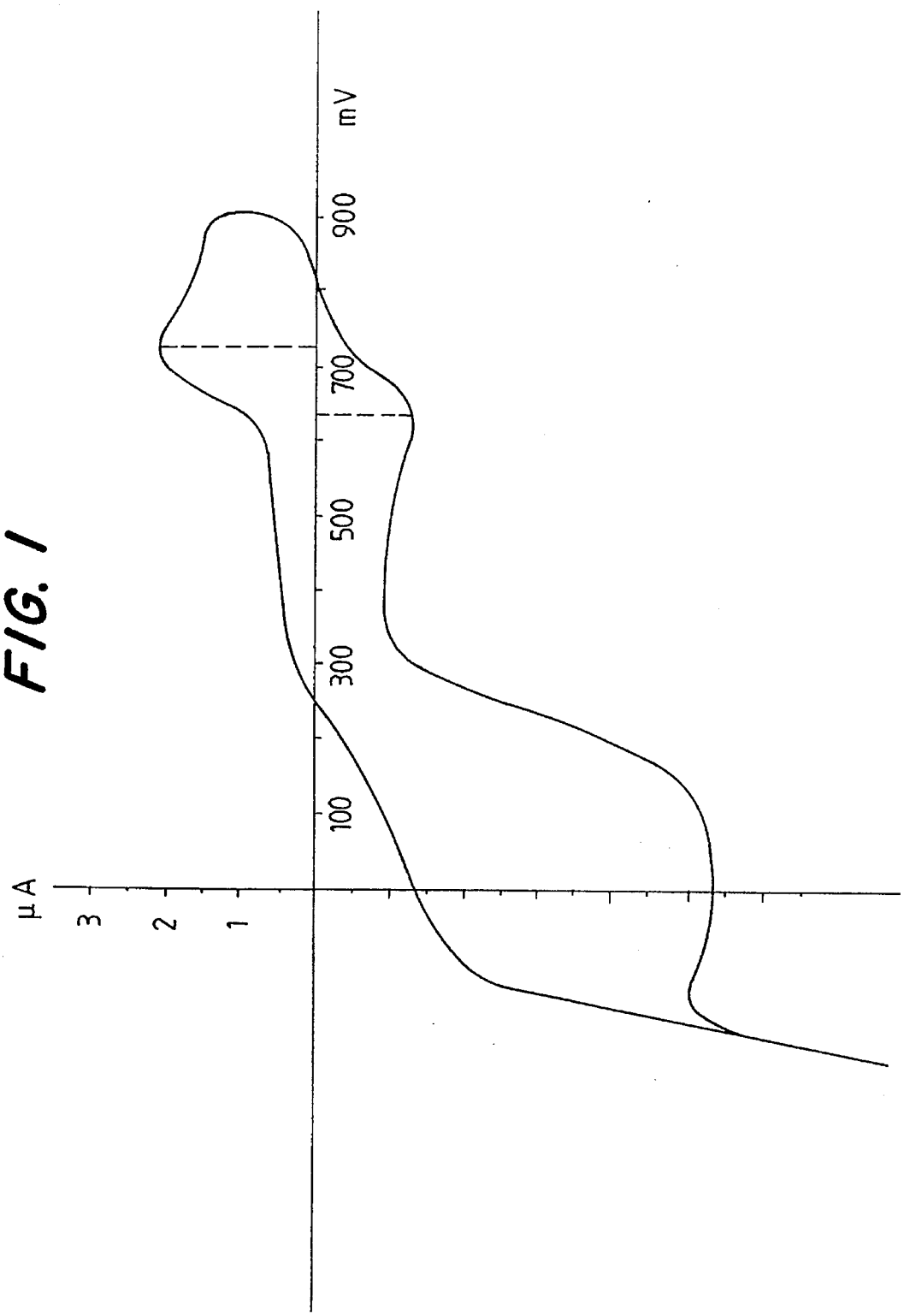
FIG. 1 a current-voltage curve for trinitrotoluene (TNT) dissolved in sulphuric acid in the case of measurement in a conventional measuring cell.

In a specific example of the process according to the invention 50 mg/l of TNT were dissolved in 10N sulphuric acid ($H_2SO_4$) and the current intensity was measured as a function of the applied voltage in a voltage range approximately 0 to 1000 mV. FIG. 1 gives the current-voltage curve for 50 mg/l of TNT in 10N sulphuric acid.

Anodic currents corresponding to electrochemical oxidation reactions are indicated in the positive Y-direction and cathodic currents, corresponding to electrochemical reductions, in the negative Y-direction. All the voltage and potential indications of the current-voltage curve (voltammogram) relate to the potential of the normal hydrogen electrode.

The given voltage range is covered in the process according to the invention with 1 V/sec, so that a measuring cycle lasts max. 2 sec.

FIG. 1 shows the result of a demonstration test with a conventional half-cell, in which the measuring electrode was an approximately 1 $cm^2$ metal plate. The starting voltage of approximately 500 mV applied to the working electrode 13 (cf. FIG. 2) was initially reduced to approximately 100 mV and the current flowing between the working electrode and a counterelectrode 14 (cf. FIG. 2) was measured as a function of the voltage applied. On reducing the starting voltage from approximately 500 to 100 mV the electrochemical reduction of TNT occurred. The nitro groups of TNT were reduced and the reduction products formed and further reference will be made thereto hereinafter. The start of the reduction of TNT is revealed by the strongly rising cathodic current below approximately 500 mV, in this case with a current maximum at approximately 100 mV. The cathodic current maximum is dependent on the environment.

On reaching the lower voltage value the voltage is raised in 1 V/sec steps to approximately 900 mV. As can be gathered from the voltammogram of FIG. 1, the current-voltage curve has an anodic current peak at approximately 700 mV for 50 mg/l of TNT. There is an oxidation of the reduction product at this voltage.

On reaching the upper voltage value of 900 mV the voltage at the working electrode is again reduced. The current-voltage curve has a cathodic current peak at approximately 600 mV. In this voltage range there has been a reduction of the reaction products formed by oxidation from the reduction products. For voltages below approximately 500 mV there is once again a reduction of the nitro groups of TNT.

The potential interval in which working takes place for the determination of nitrotoluene extends from a lower, cathodic reverse potential which, up to 300 mV, is more negative than the potential of the cathodic current maximum, to an upper, anodic reverse potential, which up to approximately 700 mV is more positive than the potential of the anodic current maximum.

The reduction product formed during the reduction of nitro groups of TNT, as can be gathered from the voltammogram, forms a redox pair readily detectable by the anodic and cathodic current peaks and by means of which the detection of TNT can take place directly in situ in a simple and rapid manner.

The current peaks of the redox pair have a different level for different TNT concentrations. The area below the current-voltage peak or the level thereof constitutes a measure for the concentration of the TNT in sulphuric acid. In order to increase the measuring accuracy, different voltage ranges can be covered.

The current-voltage curves for DNT and NT, as well as their derivatives have corresponding paths. However, the reduction of DNT, NT etc. occurs at lower voltage values than in the case of TNT. In addition, the redox pairs or systems have current peaks displaced with respect to the voltage compared with the TNT redox pair. Through a suitable superimposing of current-voltage curves in extended voltage ranges, it is possible to detect NT in the presence of DNT and TNT in a quantitative manner. Phosphoric acid can be used in place of sulphuric acid as the electrolyte. TNT-like compounds such as toluene or xylene musk, as well as the different aminotoluenes have no reaction in the selected voltage ranges, so that there is no cross-sensitivity. The process is also usable for temperature ranges of 0° to 40° C., without there being a falsification of the measured results.

Figure 2:
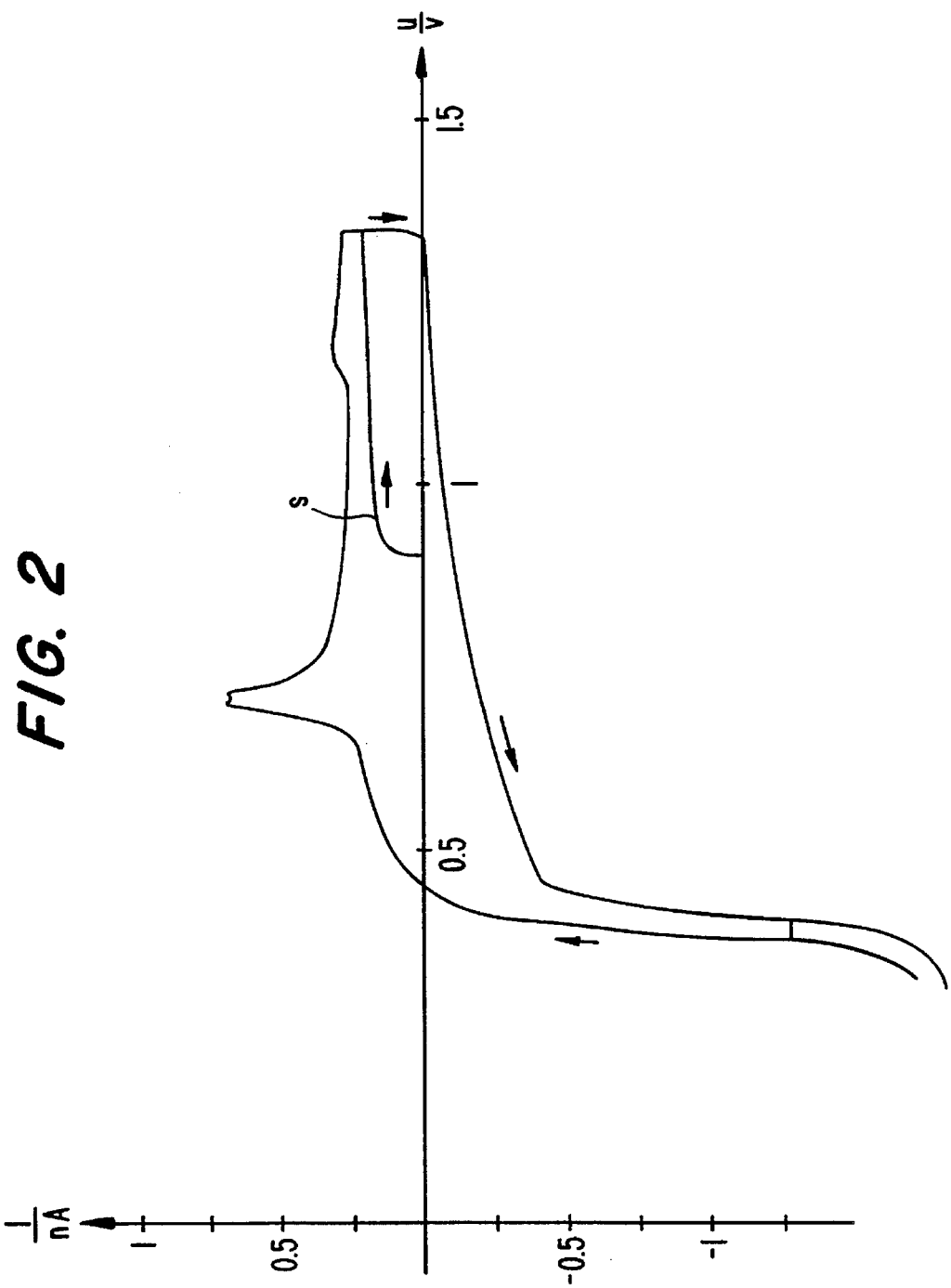
FIG. 2 a current-voltage curve for trinitrotoluene (TNT) dissolved in sulphuric acid, measured with a gold microelectrode.
Figure 3:
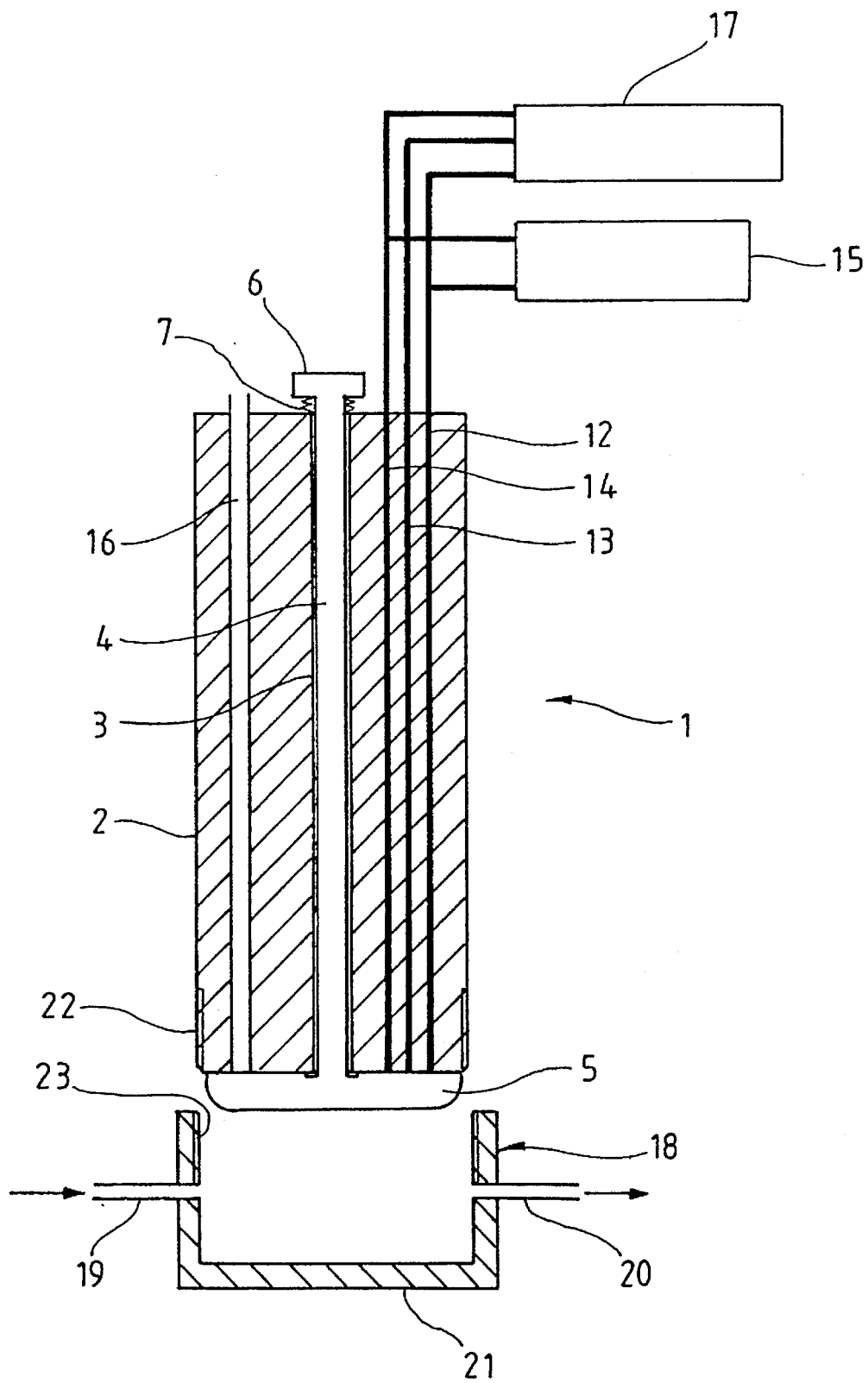
FIG. 3 a diagrammatic representation of a sensor element of the apparatus according to the invention.

FIG. 2 shows the TNT determination with the same solution as in FIG. 1, but with a gold microelectrode in the form of a wire having a diameter of approximately 25 μm in a sensor element according to FIG. 3. There are much lower currents (but higher current density). The measurement here commences in the double layer area S of the measuring electrode at a starting potential between 700 and 1000 mV. As from this point the potential of the measuring electrode (working electrode) is modified at a speed of approximately 200 mV/sec up to the upper reverse potential. The current flowing in this starting phase is exclusively the charge reversal current of the electrochemical double layer (capacitive current).

As from the upper reverse point the potential passes with the same voltage speed in the negative direction up to the lower reverse point (cathodic path) and back again to the upper reverse point (anodic path). Thus, a measuring cycle is concluded. TNT reduction takes place in a potential range below 500 mV, in which it is also possible to electrochemically reduce a plurality of substances, which can be contained in unknown soils, liquids or gases and the current flowing as a result of the TNT reduction in the potential range of 400 to 100 mV RHE has a characteristic maximum (cathodic current maximum).

The quotient of the maximum current (anodic current peak) in the anodic path and the current measured in the starting phase (capacitive current) is proportional to the TNT content.

A sensor element 1 shown in FIG. 3 has a casing 2, which is provided in its centre with a hole 3. In said hole 3 is placed a post 4, on whose lower end terminating flush with the casing 2 is arranged a scraper 5. At the end opposite to the scraper 5 the post 4 projecting out of the casing 2 has a head 6, on whose underside a spring 7 can be positioned between the head 6 and the casing 2. The spring 7 ensures that the scraper is always applied to the underside of the casing. Through the casing half 8 of the casing 2 are passed electrodes 12,13,14, namely a reference electrode 12, a working electrode 13 and a counterelectrode 14. The reference electrode 12 is a hydrogen electrode, which in the represented embodiment is a platinum pin exposed to cathodic current via a constant current source 15. Through the cathodic direct current of approximately 1 mA/cm$^2$ hydrogen is evolved at the reference electrode 12. As the resulting hydrogen/reference electrode (platinum pin) system produced has a very low overvoltage and high exchange current density, despite the cathodic polarization of the reference electrode 12 the reversible hydrogen potential virtually occurs. The working electrode 13 with which the electrochemical behaviour is to be investigated is a gold pin and to the counterelectrode 14 is connected by means of a not shown microammeter with an also not shown voltage source, preferably a d.c. voltage source of a regulating and evaluating unit 17, whose voltage can be changed in measurable manner. The counterelectrode 14 is once again a gold electrode. A special regulating device, e.g. a potentiostat, regulates the current between the working electrode and counterelectrode in such a way that the desired potential difference is obtained between the working electrode and reference electrode. The power supply of the apparatus can take place by means of a mobile supply unit, e.g. batteries, so that the portability of the apparatus is ensured.

Another construction form is constituted by the known microelectrode, whose surface is preferably also mechanically worked.

In the longitudinal side of the casing 2 opposite to the passages for the electrodes 12 to 14 is provided an electrolyte supply line 16. The electrolyte is preferably sulphuric or phosphoric acid ($H_2SO_4$, $H_3PO_4$). The gold or platinum electrodes 12,13,14 are not attacked by these acids.

For the identification of TNT, DNT, NT and derivatives thereof by means of the process according to the invention, the sensor element 1 can be immersed in a flow cell 18. The latter has an inlet 19 and an outlet 20, through which the liquid or gaseous substances to be tested can be passed through the cell 18 and past the sensor element 1. In order to be able to use the same sensor element 1 in different environments and for different substances (soils, liquids, gases), turns or coils 22,23 are provided in the lower outside of the casing 2 of the sensor element 1 and the inside of the casing 21 of the flow cell 18. In this way the upper, open flow cell 18 can, if required, be screwed onto the sensor element 1.

For the testing of gases it is possible to place below the sensor element 1 a nanoporous, hydrophobic diaphragm and on the diaphragm side remote from the sensor element is located the flow cell 18 for the gas through which the latter is pumped by means of a pump. The working electrode 12 is preferably located on the ends of the pores of the diaphragm. The size of the pores is preferably 40 nm. In order to increase the transition of TNT/DNT from the gaseous into the liquid phase, the electrolytic solution is mixed with a difficultly volatile organic co-solvent readily dissolving TNT/DNT.

The electrodes 12,13,14 of the sensor element 1 are jointly connected to the regulating and evaluating electronics 17 by means of which the concentrations of the TNT, DNT, NT and derivatives thereof can be determined from the applied voltage and the measured current values. By means of an output unit it is possible to directly read off the concentrations. There can also be an alarm unit for emitting an alarm signal on exceeding a threshold value with respect to the concentration.

Thus, a process and an apparatus are provided by means of which contaminations such as TNT, DNT, NT and derivatives thereof can be determined in an inexpensive, simple and rapid manner in soils, liquids and gases. The apparatus is usable in situ, so that the hitherto necessary one hour period between sampling and sample determination is no longer necessary. The contaminated area can be accurately demarcated, so that disposal costs can be reduced. The apparatus is still usable after being stored for many years. This ensures the safety of the persons using it, particularly when seeking mines.

We claim:

1. A process for the detection of nitrotoluenes and derivatives of nitrotoluenes in a substance comprising soil, liquid or gas, which comprises providing electrodes including a working electrode; applying a voltage to the working electrode in contact with an electrolytic solution containing the substance; during a measuring cycle reducing the voltage for producing a reduction reaction and increasing the voltage for producing an oxidation reaction; and determining at least a current intensity of a residual current and an anodic current maximum occurring during the measuring cycle as a function of the voltage applied, whereby the presence of the nitrotoluene can be detected.

2. A process according to claim 1, further comprising reducing the applied voltage on reaching a fixed, upper value, in order to produce a reduction reaction.

3. A process according to claim 2, wherein the measuring cycle is terminated on reaching a starting voltage.

4. A process according to claim 1 or 2, further comprising increasing the voltage above the value at which an anodic current maximum occurs.

5. A process according to claim 1 or 2, wherein different voltage ranges are effected during respective measuring cycles.

6. A process according to claim 5, wherein current-voltage curves of the different voltage ranges are superimposed.

7. A process according to claim 1 or 2, further comprising following a measuring cycle, reversing polarity of the electrodes several times for cleaning the working electrode.

8. A process according to claim 1 or 2, wherein a surface of the working electrode is periodically cleaned following a measuring cycle.

9. A process according to claim 8, wherein the working electrode is cleaned by a mechanical scraper or sliding wiper.

10. A process according to claim 1 or 2, wherein a working electrode is permanently cleaned by a scraper or sliding wiper.

11. A process according to claim 1 or 2, wherein an area surrounding the working electrode is acidified.

12. A process according to claim 11, wherein the substance is a liquid and is moved past a sensor element with the working electrode.

13. A process according to claim 12, wherein the liquid substance is passed through a flow cell.

14. A process according to claim 1 or 2, wherein the substance is a gas and is moved past a liquid-impermeable, but gas-permeable diaphragm through which the gaseous substance enters the electrolytic solution.

15. A process according to claim 14, wherein the gaseous substance is moved by pumping the gaseous substance past the diaphragm.

16. A process according to claim 14, wherein a co-solvent for dissolving the nitrotoluene is added to the electrolytic solution. substance to be tested is moved past a sensor element with a working electrode.

17. A process according to claim 1 or 2, wherein the electrolytic solution is heated before carrying out a measuring cycle.

18. A process for the detection of nitrotoluenes and derivatives of nitrotoluenes, in a substance comprising soil, liquid or gas, which comprises:

initially applying to an electrode in contact with an electrolytic solution containing the substance a voltage at a level relative to a hydrogen electrode at which a double layer area forms in the case of the nitrotoluenes to be determined;

increasing the voltage to a reverse potential of more than 1 V;

measuring the current intensity of a residual current obtained in the double layer area;

then reducing the voltage for producing a reduction reaction;

determining a voltage value of an occurring cathodic current maximum;

for producing an oxidation reaction, increasing the voltage again;

determining a voltage value at which an anodic current maximum occurs;

determining a current intensity of the anodic current maximum; and determining the quotient of the current intensity of the anodic current maximum and the measured current intensity of the residual current as a value representing the nitrotoluene content in the substance.

* * * * *